US007605385B2

(12) United States Patent
Bauer

(10) Patent No.: US 7,605,385 B2
(45) Date of Patent: Oct. 20, 2009

(54) ELECTRO-LESS DISCHARGE EXTREME ULTRAVIOLET LIGHT SOURCE

(75) Inventor: Bruno Bauer, Reno, NV (US)

(73) Assignee: Board of Regents of the University and Community College System of Nevada, on behlaf of the University of Nevada, Reno, NV (US)

(*) Notice: Subject to any disclaimer, the term of this patent is extended or adjusted under 35 U.S.C. 154(b) by 0 days.

(21) Appl. No.: 11/572,894

(22) PCT Filed: Jul. 28, 2005

(86) PCT No.: PCT/US2005/026796

§ 371 (c)(1),
(2), (4) Date: Jun. 24, 2008

(87) PCT Pub. No.: WO2006/015125

PCT Pub. Date: Feb. 9, 2006

(65) Prior Publication Data

US 2008/0258085 A1 Oct. 23, 2008

Related U.S. Application Data

(60) Provisional application No. 60/592,240, filed on Jul. 28, 2004.

(51) Int. Cl.
*A61N 5/06* (2006.01)
*G01J 3/10* (2006.01)
*H05G 2/00* (2006.01)

(52) U.S. Cl. ............................... 250/504 R; 250/492.2; 250/492.22; 250/493.1; 250/505.1; 378/119; 378/34; 378/124; 378/143

(58) Field of Classification Search ............. 250/504 R, 250/492.2, 492.22, 493.1, 505.1; 378/119, 378/34, 124, 143

See application file for complete search history.

(56) References Cited

U.S. PATENT DOCUMENTS

| | | | |
|---|---|---|---|
| 3,950,670 | A | 4/1976 | Hruda |
| 4,166,760 | A | 9/1979 | Fowler et al. |
| 4,277,305 | A | 7/1981 | Bohachevsky |
| 4,504,964 | A | 3/1985 | Cartz et al. |
| 4,994,715 | A | 2/1991 | Asmus et al. |
| 5,317,574 | A | 5/1994 | Wang |

(Continued)

OTHER PUBLICATIONS

PCT/US2005/026796, International Search Report and the Written Opinion, Jan. 19, 2006, 8 pages.

*Primary Examiner*—David A Vanore
*Assistant Examiner*—Meenakshi S Sahu
(74) *Attorney, Agent, or Firm*—Ryan A. Heck; UNR-DRI Technology Transfer Office

(57) ABSTRACT

An electrode-less discharge source of extreme ultraviolet (EUV) radiation (10) efficiently assembles a hot, dense, uniform, axially stable plasma column (5) with magnetic pressure and inductive current drive. It employs theta-pinch-type magnetic compression of plasma confined in a magnetic mirror. Plasma, confined in a magnetic mirror, is made to radiate by resonant magnetic compression. The device comprises a radiation-source gas input nozzle (1), an optional buffer-gas input flow (2), mirror-field coils (9*a*, 9*b*), theta-pinch coils (8*a*, 8*b*), a plasma and debris dump (11), and an evacuation port (7). The circular currents yield an axially stable plasma-magnetic-field geometry, and a reproducible, stable, highly symmetrical EUV source.

44 Claims, 6 Drawing Sheets

U.S. PATENT DOCUMENTS

| | | | |
|---|---|---|---|
| 5,335,238 | A | 8/1994 | Bahns |
| 5,656,819 | A | 8/1997 | Greenly |
| 6,007,963 | A | 12/1999 | Felter et al. |
| 6,026,099 | A | 2/2000 | Young |
| 6,167,065 | A | 12/2000 | Rocca |
| 6,172,324 | B1 | 1/2001 | Birx |
| 6,304,630 | B1 | 10/2001 | Bisschops et al. |
| 6,356,618 | B1 | 3/2002 | Fornaciari et al. |
| 6,469,310 | B1 | 10/2002 | Fiedorowicz et al. |
| 6,498,832 | B2 | 12/2002 | Spence et al. |
| 6,576,917 | B1 | 6/2003 | Silfvast |
| 6,677,600 | B2 | 1/2004 | Ikeuchi |
| 6,703,771 | B2 | 3/2004 | Becker et al. |
| 6,760,406 | B2 | 7/2004 | Hertz et al. |
| 6,788,763 | B1 | 9/2004 | Neff et al. |
| 6,804,327 | B2 | 10/2004 | Schriever et al. |
| 6,809,327 | B2 | 10/2004 | Bristol |
| 6,815,700 | B2 | 11/2004 | Melnychuk et al. |
| 6,847,044 | B2 | 1/2005 | Rice et al. |
| 6,865,255 | B2 | 3/2005 | Richardson |
| 6,885,015 | B2 | 4/2005 | Wester |
| 6,894,298 | B2 | 5/2005 | Ahmad et al. |
| 6,912,267 | B2 | 6/2005 | Orsini et al. |
| 7,180,082 | B1 * | 2/2007 | Hassanein et al. ....... 250/504 R |

* cited by examiner

ELECTRO-LESS DISCHARGE EXTREME ULTRAVIOLET LIGHT SOURCE

CROSS-REFERENCE TO RELATED APPLICATIONS

This application claims priority to co-pending PCT Patent Application Serial Number PCT/US2005/026796, filed Jul. 28, 2005, which claims priority to U.S. Provisional Patent Application Ser. No. 60/592,240, filed Jul. 28, 2004, which are hereby incorporated by reference as if set forth herein.

BACKGROUND

1. Field of the Invention

The present invention relates to a source of extreme ultraviolet (EUV) radiation. More particularly, the present invention relates to an electrode-less gas discharge device in which plasma is confined in a magnetic mirror and made to radiate by resonant magnetic compression.

2. Background

As the feature size of semiconductor devices continues to decrease, the wavelength of the light utilized in the lithographic process must also decrease accordingly. Recent developments in the semiconductor arts have created the need for a source of extreme ultraviolet (EV) light of wavelength around 13.45 nm. For example, some of the required source parameters are described in the patent by R. Bristol, "EUV source box," U.S. Pat. No. 6,809,327, Oct. 26, 2004.

Prior art methods of generating 13.45-nm EUV have included laser-produced-plasma sources and electrode-driven gas discharges. For example, the following patents disclose laser-produced plasmas: U.S. Pat. No. 6,304,630 to Bisschops, et al.; U.S. Pat. No. 6,007,963 to Felter, et al.; U.S. Pat. No. 6,469,310 to Fiedorowicz, et al.; U.S. Pat. No. 6,760,406 to Hertz, et al.; U.S. Pat. No. 6,912,267 to Orsini, et al.; U.S. Pat. No. 6,865,255 to Richardson.

Likewise, the following patents disclose electrode-driven gas discharges: U.S. Pat. No. 6,894,298 to Ahmad, et al.; U.S. Pat. No. 4,994,715 to Asmus, et al.; U.S. Pat. No. 5,335,238 to Bahns; U.S. Pat. No. 6,703,771 to Becker, et al.; U.S. Pat. No. 6,172,324 to Birx; U.S. Pat. No. 4,504,964 to Cartz, et al.; U.S. Pat. No. 6,356,618 to Fornaciari, et al.; U.S. Pat. No. 6,677,600 to Ikeuchi; U.S. Pat. No. 6,815,700 to Melnychuk, et al.; U.S. Pat. No. 6,788,763 to Neff, et al.; U.S. Pat. No. 6,167,065 to Rocca; U.S. Pat. No. 6,804,327 to Schriever, et al.; U.S. Pat. No. 6,576,917 to Silfvast; U.S. Pat. No. 6,498,832 to Spence, et al.; U.S. Pat. No. 5,317,574 to Wang; U.S. Pat. No. 6,026,099 to Young.

Laser systems have drawbacks including a high power requirement and a high cost of ownership. Gas discharges, on the other hand, are inexpensive and efficient. However, electrode-driven gas discharges will not likely meet the requirements of long lifetime, clean (essentially debris-free) operation, and stability. As is known in the art, electrodes are eroded by adjacent plasma, creating debris and limiting lifetime. Furthermore, parallel currents yield an unstable plasma-magnetic-field geometry, limiting reproducibility.

The present invention overcomes the disadvantages and limitations of the prior art by efficiently assembling a hot, dense, uniform, axially stable plasma column with magnetic pressure and inductive current drive. It employs theta-pinch-type compression of plasma confined in a magnetic mirror. The following patents disclose related prior art: I. O. Bohachevsky, "Beam heated linear theta-pinch device for producing hot plasmas," U.S. Pat. No. 4,277,305, Jul. 7, 1981. In this and other linear theta-pinches, the plasma is heated by magnetic compression, but it is not confined axially, nor prevented from impacting its cylindrical container when the magnetic field drops. K. Fowler, et al., "Plasma confinement apparatus using solenoidal and mirror coils," U.S. Pat. No. 4,166,760, Sep. 4, 1979. In this and other mirror machines, magnetic mirrors are used to confine electrons and ions at low densities, in large volumes. There is no buffer plasma to isolate the wall, nor unequal mirror strengths to make plasma flow to a debris dump. R. M. Hruda, "Electrodeless discharge adaptor system," U.S. Pat. No. 3,950,670, Apr. 13, 1976. In this and other electrode-less plasma discharges, high frequency changing magnetic fields induce curling electric fields that ionize gas and drive currents. However, the plasma is not magnetically confined, nor heated by magnetic compression, nor made to magneto-acoustically resonate with the driving field.

In addition, preferred embodiments of the present invention would utilize specialized materials and auxiliary systems, such as are disclosed, for example, in the following patents: B. J. Rice, et al. "Electrical discharge gas plasma EUV source insulator components," U.S. Pat. No. 6,847,044, Jan. 25, 2005; N. Wester, "Thermionic-cathode for pre-ionization of an extreme ultraviolet (EUV) source supply," U.S. Pat. No. 6,885,015, Apr. 26, 2005.

SUMMARY

The present invention comprises an EUV radiation source that is clean, long-lived, efficient, and capable of producing a broad range of wavelengths and intensities of radiation from a small volume. The source may be used to provide radiation for a wide variety of applications, such as, but not limited to, integrated circuit lithography, annealing of materials, spectroscopy, microscopy, plasma diagnostics, etc. The spatial, angular, and temporal profiles of the emitted radiation can be tailored to the application.

The EUV radiation source comprises a radiation-source-material input nozzle, an optional buffer-gas input flow, mirror-field and theta-pinch magnet coils, a plasma and debris dump, and an evacuation port. Plasma, confined in a magnetic mirror, is made to radiate by resonant magnetic compression. The circular currents yield an axially stable plasma-magnetic-field geometry, and a reproducible, stable, symmetrical EUV source. Source cleanliness and long life are promoted by the absence of electrodes and by the isolation of the plasma from the walls by distance, buffer plasma, and intense magnetic field.

The mirror magnetic field that repeatedly contracts and expands can be made using a variety of configurations of magnet coils, magnetic materials, and permanent magnets. A simple and often practical way is to have one set of coils for each of the two major functions: mirror-field coils to create the overall magnetic geometry and theta-pinch coils to make the mirror field contract and expand. This implementation is the main one described here.

The mirror-field coils carry a steady (or slowly changing) current that produces a mirror-geometry magnetic field, i.e., one in which the magnetic field is several times greater at the device ends than at the device midplane. This magnetic-mirror field confines the plasma. This field is made somewhat axially asymmetrical, to make the plasma confinement better toward the input nozzle than toward the plasma and debris dump, so that plasma flows gently to the plasma and debris dump and the evacuation port. This reduces the amount of optics-damaging debris that leaves the device (e.g., to the intermediate focus of a microlithography station).

The theta-pinch coils carry a rapidly changing (e.g., pulsed, oscillating, etc.) current, to make a rapidly changing mirror-geometry magnetic field that induces oppositely directed currents in the plasma and alternately compresses and expands the plasma. The magnetic pumping and theta-pinch compression effectively heat the plasma and make it dense, so that it radiates efficiently. The theta-pinch coils are part of a circuit capable of efficiently driving a large current, such as a radio-frequency-driven, resonant LC-tank circuit. The oscillation or pulse frequency is typically tuned to the natural plasma bounce frequency to enhance the plasma oscillation and compression.

The radiation output is through a large solid angle opening, allowing EUV-transport optics to transfer a significant effective total collecting solid angle of radiation from the plasma to a real EUV image source outside the plasma.

Greater efficiency (radiation output to electrical input) is anticipated for the continuously driven plasma source described here, than for prior-art repetitive sources in which the plasma is discarded after each radiation burst. There are several reasons for this. First, the quasi-spherical implosion and resonance results in less lost plasma translational energy. Second, the reutilization of multicharged ions spreads the significant energy cost of ionization over several EUV emission cycles. Last, some energy can be recovered from the plasma each cycle by the electrical circuit.

BRIEF DESCRIPTION OF THE DRAWING FIGURES

DETAILED DESCRIPTION

Figure 1:
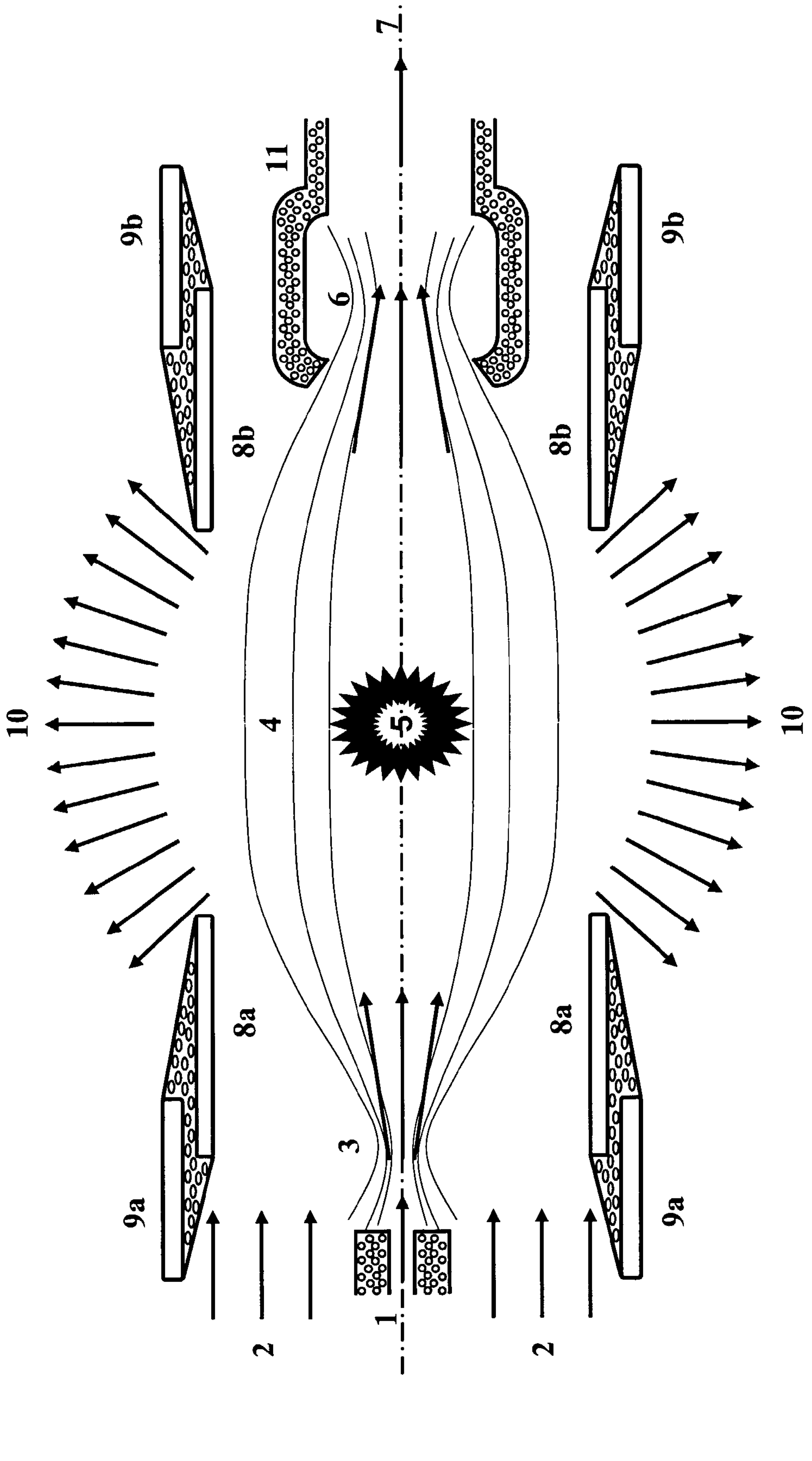
FIG. 1 is a conceptual diagram of an electrode-less light source configured in accordance with the teachings of this disclosure.

Persons of ordinary skill in the art will realize that the following description is illustrative only and not in any way limiting. Other modifications and improvements will readily suggest themselves to such skilled persons having the benefit of this disclosure. In the following description, like reference numerals refer to like elements throughout.

In general, the device of disclosure produces radiation by confining and controlling an ionized working fluid, known as plasma, using a magnetic field. The plasma is repeatedly imploded, made to radiate, and expanded. This cycle recurs continuously, up to millions of times per second, for an extended period, such as 1 year.

FIG. 1 discloses a schematic side diagram of the device comprising one aspect configured in accordance with the teachings of this disclosure. The device is cylindrically symmetric about an axis indicated by a dashed line (which goes from the reference numeral 1 to the reference numeral 7). As used herein, this axis is referred to as the "z" axis or the "axial" direction. The "radial" or "r" coordinate is orthogonal to the z-axis. The center of the device may be defined by the coordinates (r,z)=(0,0).

As shown in FIG. 1, the device comprises a radiation-source-material input nozzle 1, an optional buffer-gas input flow 2, a mirror-magnetic-field confined plasma from reference numeral 3 to reference numeral 6, magnetic field 4, a hot, dense radiating plasma 5, an evacuation port 7, theta-pinch coils 8*a* and 8*b*, mirror-field coils 9*a* and 9*b*, radiation output 10 (to EUV reflectors, not shown), and a mirror-throat plasma and debris dump 11. The entire device is in a vacuum vessel (not shown). The input nozzle 1 is disposed within the vessel along the z-axis, the input nozzle being configured to input material along the z-axis. The flow of material through and from the input nozzle 1 is shown with arrows near the reference numerals 1 and 3. The optional buffer-gas input flow 2 is disposed radially about the z-axis at a larger radius than the input nozzle 1. The flow of material from the optional buffer-gas input flow 2 is shown with arrows near the reference numerals 2. The evacuation port 7 is disposed along the z-axis and spaced apart from the input nozzle 1. The flow of material into the evacuation port 7 is shown with arrows near the reference numerals 6 and 7. The first theta-pinch coil 8*a* is disposed radially about the axis proximate to the input nozzle 1. The second theta-pinch coil is disposed radially about the axis proximate to the evacuation port 7. The first mirror-field coil 9*a* is disposed radially about the axis proximate to the input nozzle 1. The second mirror-field coil 9*b* is disposed radially about the axis proximate to the evacuation port 7. The first and second mirror-field coils 9*a* and 9*b* are positioned and driven so as to produce a magnetic field with a magnetic mirror confinement geometry, as well known in the art. The magnetic field 4 from the mirror field coils 9*a* and 9*b* confines the plasma 5. The first and second theta pinch coils 8*a* and 8*b* are positioned and driven so as to produce an additional magnetic field with a magnetic mirror confinement geometry, that strengthens or weakens the mirror field produced by the mirror-field coils 9*a* and 9*b*. The first theta-pinch coil 8*a* is disposed between the first mirror-field coil 9*a* and the z-axis, and the second theta-pinch coil 8*b* is disposed between the second mirror-field coil 9*b* and the z-axis. The theta-pinch coils are interior to the mirror-field coils so that the fast changing magnetic flux from the theta-pinch coils does not need to diffuse through the mirror-field coils. The first and second theta pinch coils 8*a* and 8*b* and the first and second mirror-field coils 9*a* and 9*b* are driven so as to form and heat a plasma 5 about a position midway between the input nozzle and the evacuation port, thereby emitting radiation at the midway position.

To minimize debris and promote component life, plasma-facing components may be treated or coated with plasma-resistant materials, such as, but not limited to, diamond, boron, etc., as known in the art.

The mirror magnetic field that repeatedly contracts and expands, confining and controlling the plasma, can be made using a variety of configurations of magnet coils, magnetic materials, and permanent magnets, as is known in the art. For example, at one extreme, such a magnetic field can be produced by a single coil, with appropriate location and spacing of windings, driven by a current that has both slowly and rapidly changing aspects (e.g., an oscillating current added to a dc current). At the other extreme, such a magnetic field can be produced using a large number of coils and magnets. For simplicity of description, the main configuration described here has one set of coils for each of the two major functions: mirror-field coils 9*a* and 9*b* to create the overall magnetic geometry and theta-pinch coils 8*a* and 8*b* to make the mirror field contract and expand. Such a division is also often practical, when electrical drive, cooling, manufacturing cost, maintenance, etc. are considered in the design.

As an illustrative example, a particular device will be described here that has a radius and length of approximately 1 cm and 4 cm, respectively. These and all specifications given below are approximate, as the size and proportions of the device will vary with the application. As is known in the art, such a plasma confinement and heating device can be made orders of magnitude bigger or smaller, with approximately proportional scaling of most components, and scaling of other device parameters following the known laws of physics (e.g., the theta-pinch drive pulse duration is proportional to size but the drive energy is proportional to volume).

Figure 2:
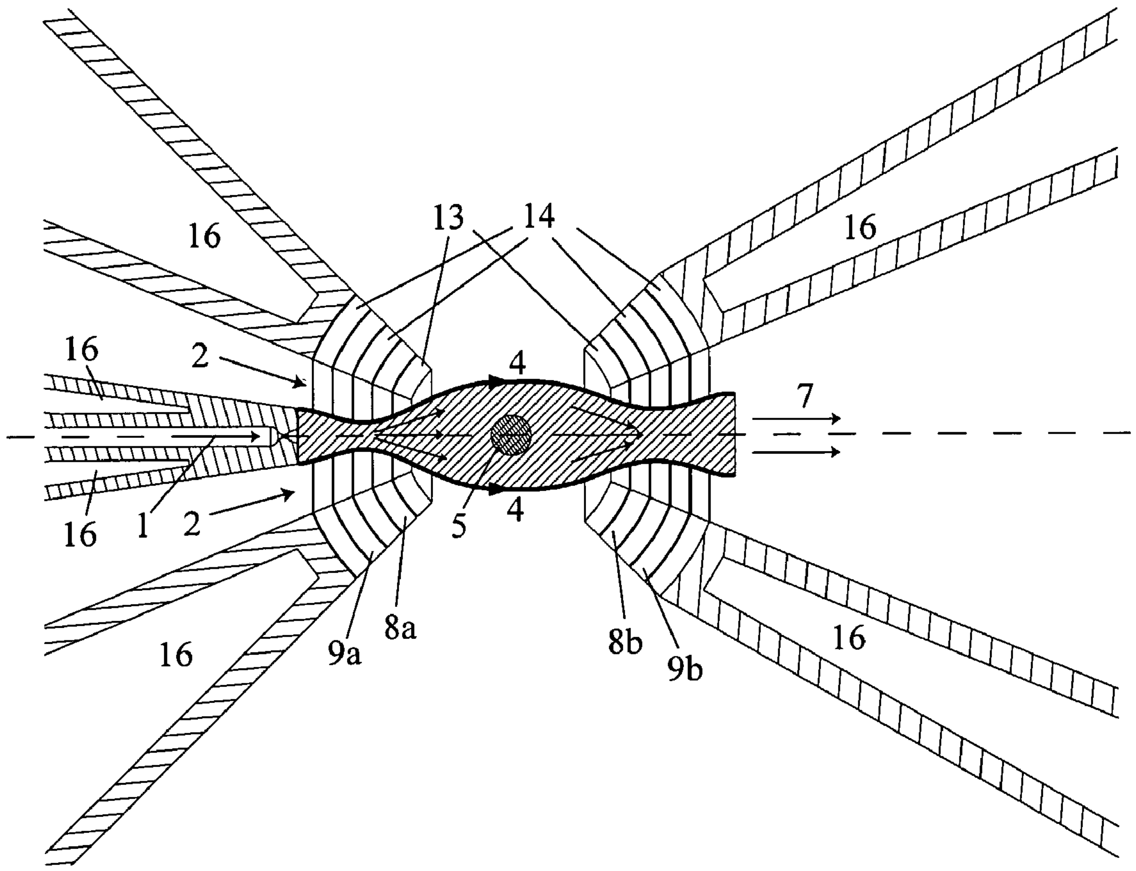
FIG. 2 is a drawing of a mechanically integrated embodiment of an electrode-less light source configured in accordance with the teachings of this disclosure. It shows the near-plasma-portion of the device.

The device is supported by mechanical mounts and powered by electrical connections as is known in the art. FIG. 2 shows a mechanically integrated embodiment of the device. This drawing shows a cross-sectional view of the portion of the source near the plasma. As in FIG. 1, the device is cylindrically symmetric about the z-axis, indicated by a dashed line. Once again are shown the radiation-source-material input nozzle 1, the optional buffer-gas input flow 2, the mirror-magnetic-field confined plasma, the magnetic field 4, the hot, dense radiating plasma 5, the evacuation port 7, the theta-pinch coils 8*a* and 8*b*, and the mirror-field coils 9*a* and 9*b*. As before, the flow of material is shown with arrows near reference numerals 1, 2, 5, and 7. In addition, the device comprises plasma and heat shields 13, insulation 14, and cooling channels 16 (e.g., for water). The two plasma and heat shields 13 are disposed radially about the z-axis, between the theta-pinch coils 8*a* and 8*b* and the plasma. The plasma and heat shields 13 face the plasma and are useful for decreasing the thermal load to the current carrying coils 8*a*, 8*b*, 9*a*, and 9*b* and for minimizing debris. As known in the art, they can be made out of refractory material and/or have a plasma-resistant coating, as described above. The insulation 14 is disposed radially about the z-axis, electrically isolating the coils 8*a*, 8*b*, 9*a*, and 9*b*. The outer parts outside the cooling channels 16 serve as a support structure and provide power and cooling to the coils 8*a*, 8*b*, 9*a*, and 9*b* and the shields 13. In this illustrative embodiment, the mirror-throat plasma and debris dump are simply an open cone to the evacuation port 7.

The device may be operated in a vacuum-tight chamber, using vacuum feedthroughs, vacuum pumps, and sensors or instruments, well known in the art, that monitor device input and output parameters, such as, but not limited to, gas pressure, gas composition, EUV radiation intensity, EUV spectrum, magnetic field, plasma conditions, etc.

In a preferred embodiment, the device further comprises heat pipes for cooling the theta-pinch coils, the mirror coils, the input nozzle, the evacuation port, and/or other source components. Through these pipes flows coolant, such as, but not limited to, water, liquid metal, liquid nitrogen, helium, etc., as is known in the art. The pipes may be connected to regions, as are known in the art, that are structured for high heat removal, such as, but not limited to, microchannels and/or porous, high-thermal-conductivity heat-exchange matrix. In addition to removing energy deposited by Ohmic heating, damage to plasma-facing surfaces by radiation is of particular concern in a high intensity source, and several kW/cm$^2$ would preferably be removed from these surfaces. Such cooled regions are indicated in FIG. 1 by a fill pattern consisting of many small circles.

Figure 3:
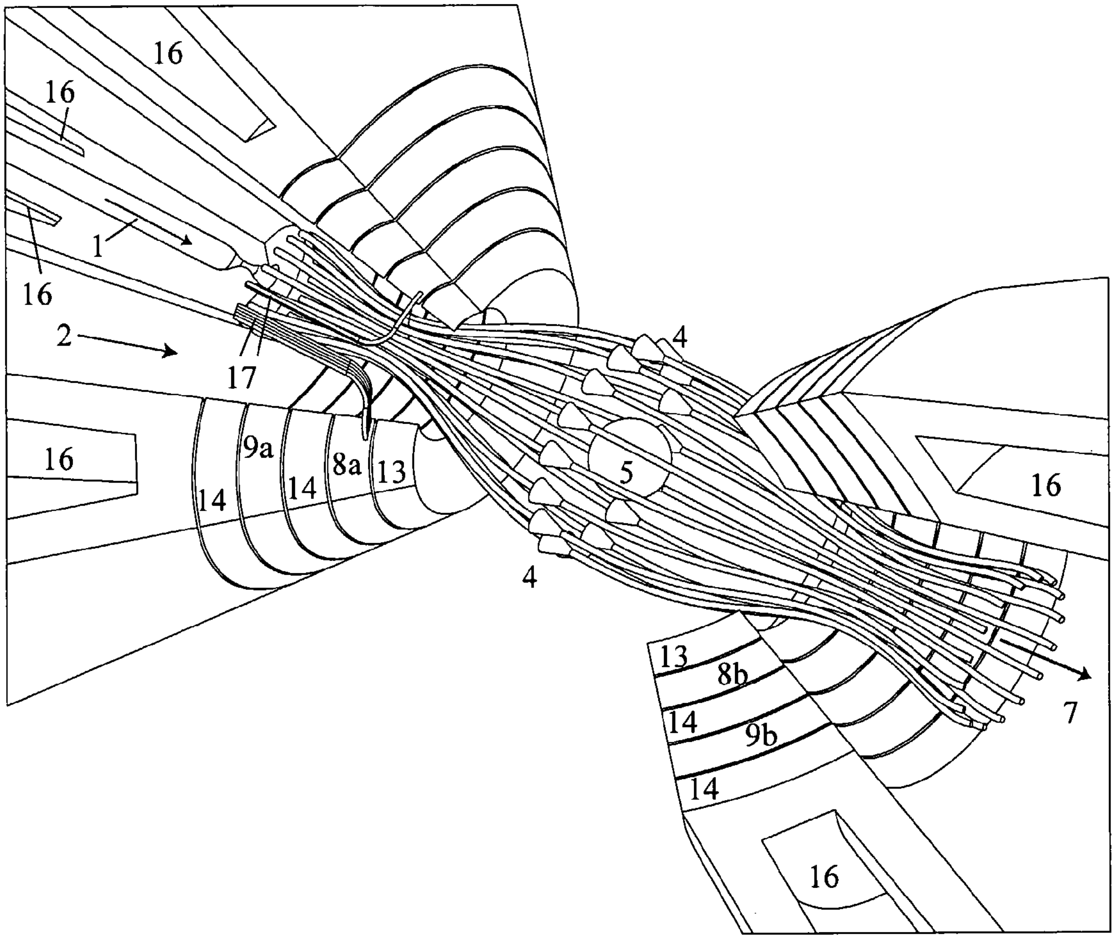
FIG. 3 is a 3-D cutaway perspective showing details of the components near the plasma, including microchannel cooling.

The option of microchannel cooling is shown in greater detail in FIG. 3. FIG. 3 is a 3-D cutaway perspective of the mechanically integrated embodiment shown in FIG. 2. As before, it comprises a radiation-source-material input nozzle 1, an optional buffer-gas input flow 2, magnetic field 4, a hot, dense radiating plasma 5, an evacuation port 7, theta-pinch coils 8*a* and 8*b*, mirror-field coils 9*a* and 9*b*, plasma and heat shields 13, insulation 14, and cooling channels 16. In addition, capillary cooling channels 17 are shown. Support structures with cooling channels 16 hold the magnetic coils and shields. On the left-hand-side of this figure gas (e.g., xenon) enters through a cooled Laval gas nozzle 1 and is injected toward the dense plasma region 5. The optional buffer gas 2 (e.g., helium) is injected through the space provided by the outer support structure and the input nozzle 1. Further cooling is provided by additional capillary tubing 17 that is shown embedded in the left rf field coil 8*a* and is also in the exit rf field coil 8*b* (but not shown). The shields 13 and mirror coils 9*a* and 9*b* can also be equipped with capillary coiling. The magnetic field 4 from the mirror field coils 9*a* and 9*b* confines the plasma 5. The plasma exhaust 7 is removed by a vacuum pump through the right-hand-side support structure.

In operation, the radiation-source-material input nozzle 1 injects material from which radiation is desired. The wavelengths and intensity of the emitted radiation are tailored by the choice of the material, as is well known in the art. For example, materials comprising or containing xenon (Xe), tin (Sn), or lithium (Li) can be used to produce 13-nm wavelength EUV radiation.

The device can be operated with the radiation-source material injected by the radiation-source-material input nozzle 1 in any state, e.g., as gas, as clusters of atoms or molecules, as a sol (e.g., aerosol), as dust, as a liquid jet or droplets, as solid pellets, or as plasma. The EUV source can be operated with the injected radiation-source material at a wide range of pressures and densities. The convenience of the various states for the injected matter depends on which radiation-source material is selected. All of the states can be injected in a highly directional manner (although some more than others). This is advantageous for placing the radiation-source-material input nozzle further from the plasma, to minimize debris.

In an illustrative embodiment, the radiation-source-material input nozzle 1 injects a fine (e.g., sub-mm-diameter) jet of a gas. Appropriate gas flow characteristics are selected through the choice of the input nozzle and associated gas handling equipment, as is known in the art. For example, a Laval nozzle provides a directed, supersonic flow of gas. This is useful for maximizing the distance of the nozzle tip from the central radiating region while providing a high rate of gas flow to the plasma. As an additional, complementary example, it may be useful to control the temporal evolution of the gas flow, for example, through the use of a dynamic gas puff valve. This can provide feedback control of the gas pressure and/or a burst of gas pressure. The latter is useful for providing a high central gas pressure while maintaining low pressure at peripheral locations, avoiding undesired plasma formation (arcing) at peripheral elements subjected to high voltages, such as the theta-pinch feedthroughs. A dynamic gas puff valve can used in combination with a Laval nozzle or other nozzle, by placing it upstream from the nozzle.

In an alternate illustrative embodiment, the radiation-source-material input nozzle 1 injects plasma created from solid, liquid, or porous material by a laser, a magnetron, or other sputtering source, as is known in the art. For example, a collimated plasma jet is formed by laser light (e.g., from a ns-pulsed, MW-power Nd:glass laser) focused (e.g., to a sub-mm spot) on a concave conical surface. The concave conical surface is maintained over many laser pulses by forming it from many fine wires (e.g., tin) that are slowly advanced.

The description that follows here is of an illustrative embodiment in which xenon is used to deliver, to an intermediate focus, 115 W of EUV radiation in the 2% wavelength band centered on 13.45 nm, for semiconductor microlithography. In this illustrative embodiment, the xenon flow rate is set to yield a xenon pressure of 0.01 torr at 20 degrees C. at the center of the device. This corresponds to a xenon neutral density of $3\times10^{14}$ $cm^{-3}$. Other gases and environments may be used to produce different wavelengths as desired.

The xenon is ionized as it exits the nozzle 1 by the radiation from the plasma between 3 and 6. The ionized xenon jet expands from sub-mm radius to approximately 3-mm radius at the center of the device.

When the device is initially turned on, the mechanism of xenon ionization is different, as no plasma radiation is present. In that case, the xenon gas is ionized by the induced electric fields of the theta-pinch coils 8*a* and 8*b*. Alternatively, the plasma may be initiated with an auxiliary source of photons, electrons, or electric field, such as, but not limited to, a high-voltage pin, an electron beam, a laser, a radio-frequency source, an ultraviolet light source, etc.

As an additional option, as is known in the art, a pre-ionization system may be used continuously (repetitively), to partially ionize the input material, converting it into plasma as it is injected into the central volume. This preionizer would comprise a source of photons, electrons, or electric field, such as, but not limited to, a high-voltage pin, an electron beam, a laser, a radio-frequency source, an ultraviolet light source, etc. The preionizer can be built into a package surrounding the radiation radiation-source-material input nozzle 1. Pre-ionization of the material would reduce the peak power required of the electrical driver for the theta-pinch coils 8*a* and 8*b*, if that peak power is determined by the need to initiate plasma when the device is initially turned on or when the plasma-implosion cycle is operated at low frequency. In addition, pre-ionization could be used to make a more directional plasma jet, if necessary, and to improve EUV source reproducibility, by providing the same preferred initial state for each plasma implosion.

In order to tailor the shape of the magnetic field, a device for producing a magnetic field may be included in a package surrounding the radiation-source-material input nozzle 1. Such a device preferably comprises a current-carrying coil and/or ferromagnetic material and/or permanent magnets and is preferably configured to intensify the magnetic field at the nozzle 1 and around the mirror throat 3, thereby inhibiting backflow of plasma from the hot radiation source 5 to the nozzle 1. Likewise, such a device to produce magnetic field may also be incorporated into a package surrounding the plasma and debris dump 11.

The optional buffer-gas input flow 2 injects a gas that is transparent to the desired radiation, e.g., helium (He) for 13-nm EUV radiation. Helium and the other noble gases have the advantage of not being chemically reactive. In an illustrative embodiment, the helium flow rate is set to yield a helium pressure of approximately 0.01 torr (at 20 degrees C.) in the device. This corresponds to a helium neutral density of $3\times10^{14}$ $cm^{-3}$. The helium may be ionized by similar processes and/or methods as are used to ionize the xenon gas. Helium ions collisionally confine radiation-source xenon ions, reducing EUV absorption by stray xenon in region 10, and reducing debris caused by the interaction of multicharged xenon ions (e.g., $Xe^{10+}$) with the surfaces of 8*a* and 8*b*. In addition, the low collisionality, and therefore low resistivity, of the helium plasma reduces magnetic field diffusion through the plasma, thereby improving the confinement and control (compression/expansion) of the helium-xenon plasma by magnetic fields.

The mirror-field coils 9*a* and 9*b* carry a steady (or slowly changing) current that produces a mirror-geometry magnetic field. In an illustrative embodiment, these coils produce a magnetic field of intensity 0.3 T at the device midplane (z=0) 4. A stronger field of approximately 0.6 T may be generated at the magnetic mirror necks, thereby forming a magnetic-mirror field that confines the helium-xenon plasma. If needed, much stronger magnetic fields may be generated, as is well known in the art. Also, if high electrical efficiency and low Ohmic heating are needed, the mirror-field coils can be superconducting, as is known in the art.

This field is further made somewhat axially asymmetrical, as shown in FIG. 1, by having coil 9*a* produce a more intense magnetic field (e.g., by having more turns or carrying more current) than coil 9*b*. Thus the plasma confinement is better on the left mirror throat 3 than on the right mirror throat 6, resulting in plasma flowing to the mirror-throat plasma and debris dump 11 and exiting through the evacuation port 7.

This slow but steady plasma flow to the plasma and debris dump 11 reduces the debris that leaves the device (to the intermediate focus). The mirror-throat plasma and debris dump 11 open away from the plasma, decreasing the number of particles that diffuse back from the dump to the plasma. The debris dump 11 may be in the shape of a cavity, as in FIG. 1, or may simply be an open cone connecting to the evacuation system, as in FIG. 2. The more elaborate shape of FIG. 1 is useful for reducing mirror plasma instabilities by electrically grounding the plasma magnetic field lines, which run into the dump cavity wall. It is also useful for reducing the number of multicharged ions and sputtered atoms that go to the evacuation system.

Figure 4:
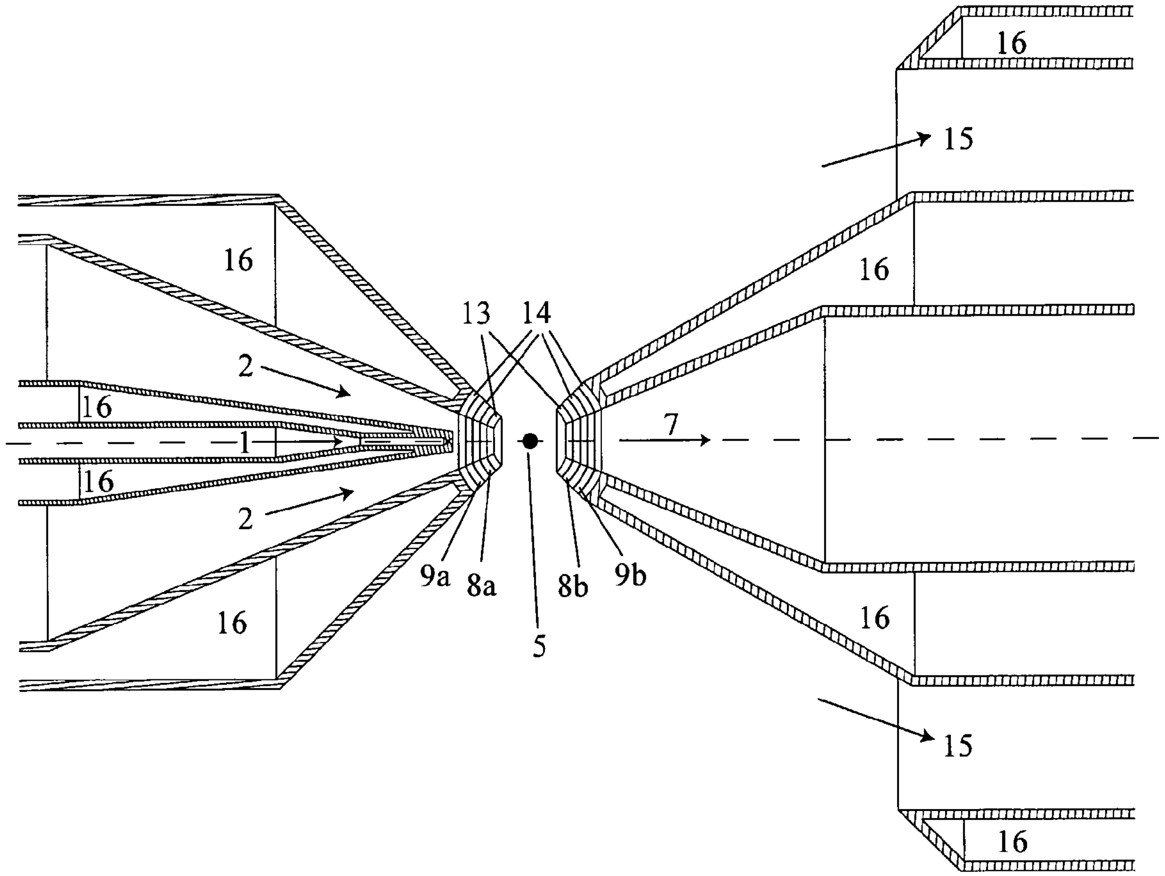
FIG. 4 is a drawing at less magnification than FIG. 2 that provides an overview of the material input and debris evacuation sections.
Figure 5:
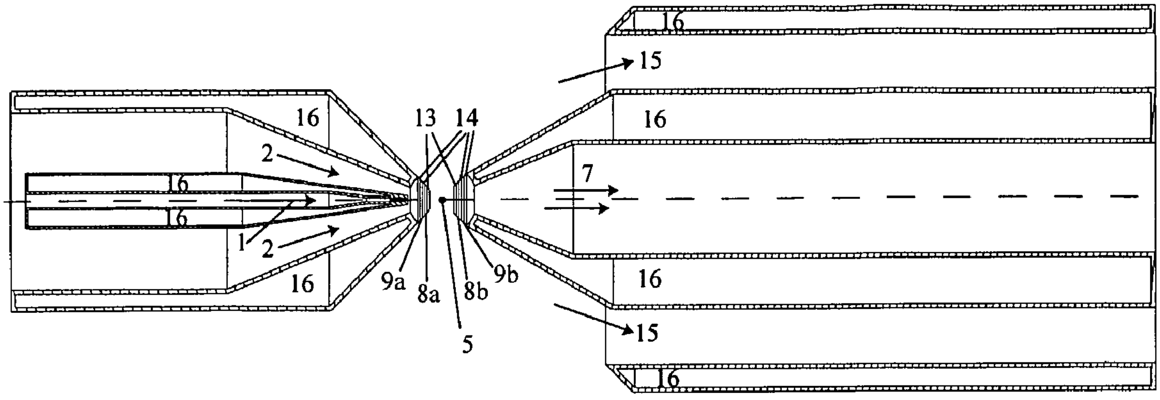
FIG. 5 is a drawing at less magnification than FIG. 4 that provides an broader overview of the material input and debris evacuation sections.

FIG. 4 and FIG. 5 give an overview of the material input and debris evacuation sections. They disclose a cross-sectional view of a solid model, views of which were disclosed in FIG. 2 and FIG. 3. FIG. 4 is a drawing of the mechanically integrated embodiment shown in FIG. 2, but at less magnification than FIG. 2, while FIG. 5 is at still lower magnification. As in FIG. 1, the device is cylindrically symmetric about the z-axis, indicated by a dashed line. As before, FIG. 4 and FIG. 5 show the radiation-source-material input nozzle 1, the optional buffer-gas input flow 2, the hot, dense radiating plasma 5, the evacuation port 7, the theta-pinch coils 8*a* and 8*b*, the mirror-field coils 9*a* and 9*b*, the plasma and heat shields 13, insulation 14, and cooling channels 16. In addition, an additional optional evacuation port 15 is shown. The support structure for the coils 8*a*, 8*b*, 9*a*, and 9*b*, insulation 14, and shields 13 are shaped conically around the z-axis such that the heat shields 13 take most of the heat load (such as radiation) from the plasma core 5. The tip of the nozzle 1 may also be equipped with a heat shield and with capillary cooling. This figure also shows an additional cooled 16 evacuation port 15. This port is disposed radially outside of the support structure of the evacuation port 7.

Axial currents carried by Ioffe bars as is known in the art may be added to impart azimuthal magnetic field variation, if improved stability of the mirror-field-confined plasma is needed. The plasma confinement time is a few microseconds, many times longer than the plasma oscillation period.

In an illustrative embodiment, the theta-pinch coils 8*a* and 8*b* are single-turn (or few-turn) coils of radius 0.7 cm and axial length 1 cm. They are insulated from the plasma, and carry a rapidly changing or pulsed current. This creates a rapidly changing mirror-geometry magnetic field that induces oppositely directed currents in the plasma and alternately compresses and expands the plasma. The magnetic pumping and theta-pinch compression effectively heat the plasma and make it dense, resulting in efficient radiating, as will be further described below.

The theta-pinch coil package may include electrostatic shielding, both inside and outside the coil, as is known in the art. The shielding would confine electromagnetic waves from the coil and could permit operation at frequencies other than those approved by the FCC for industrial applications (6.78 MHz, 13.56 MHz, etc.). The shielding would also greatly reduce capacitive coupling of the coil to the plasma. This would reduce plasma losses to walls and the generation of energetic particles, thereby increasing the cleanliness and efficiency of the EUV source. The shield inside the coil would also reduce the plasma heat load on the coil, allowing greater rf power to the coil for the same coil cooling rate.

The radiation output 10 is through an opening of 3π sr solid angle provided in the device. EUV-transport optics may be provided to transfer a significant effective total collecting solid angle of radiation, e.g., π sr, from the plasma to a real EUV image source outside the plasma, such as the intermediate focus. The EUV image source can be a small, spatially fixed point, or can have a different shape and size, as needed.

A variety of choices for EUV-transport optics may be employed. Examples may include multilayer mirrors and collections of smooth-walled capillaries or other grazing-incidence reflectors. Capillary optics have the advantage of stopping residual debris and plasma ions, and, by differential pumping and/or flow-through of helium buffer gas, of minimizing absorption of EUV by stray xenon gas. The choice of EUV optics may be optimized for the intended application.

The device will typically incorporate debris and/or spectral filters, in the direction of EUV collection, as are known in the art, such as, but not limited to, thin membranes, gas jets, plasmas, and capillaries that are differentially pumped and/or contain buffer gas.

The theta-pinch coils **8*a* and 8*b*** may comprise a radiofrequency-driven, resonant-LC circuit, or other circuitry capable of efficiently driving a large current. The theta-pinch current pulse shape can be adjusted to maximize the plasma compression, following principles known in the art, such as making the rise time of the pulse correspond to the compression time of the plasma. The theta-pinch coils may be driven at a frequency approved by the FCC for industrial applications (6.78 MHz, 13.56 MHz, etc.), or may be driven at other frequencies, with appropriate shielding. Optimally, the theta-pinch coils are constructed so as to have a high quality factor Q, using means known in the art, such as, but not limited to, use of litzendraht conductor (litz wire) and/or a helical resonator. For maximum electrical efficiency, as is known in the art, the circuit that drives the theta-pinch coils can recover energy reflected from the theta-pinch coils and/or generated by the plasma expansion after compression.

To continue the illustrative example started above, the description here assumes the coils are rf-driven to produce a 3-MHz alternating 0.18-T magnetic field in the device center. Calculations (below) indicate this suffices to deliver 115 W of 13.45 nm EUV radiation to an intermediate focus. Alternatively, if necessary, a pulsed magnetic field of several tesla can be generated. The alternating 0.18 T field adds to the steady mirror magnetic field (0.3 T in the device center), resulting in a total magnetic field that swings from 0.12 T to 0.48 T and back again, in the device center. When the magnetic field rises, the contained plasma is crushed and heated. The geometry and variation of the magnetic field is chosen to produce a quasi-spherical compression of approximately 4 (=[0.48 T]/[0.12 T]) in radius.

Although spherical compression produces the greatest density increase, compressions that are shaped otherwise also yield radiation. This is useful for obtaining a radiation source that is not point-like. The shape of the plasma compression is selected through the choice of the shape of the applied magnetic field. For example, cylindrical, quasi-cylindrical, or pancake-like compressions of the plasma may be used to obtain radiation sources in the shape of a line, a line segment, or a disk, respectively. Moreover, a mirror-plasma-shaped radiation source can be made by operating the source in a regime in which the ratio of theta-pinch heating power to plasma mass is such that Ohmic heating of the plasma exceeds compressional heating. In that case, the plasma will not change shape much but will be heated and emit radiation with an emissivity proportional to the square of the plasma density.

Returning to the above illustrative embodiment with quasi-spherical compression, the 4-fold reduction in radius is estimated to produce a factor of approximately 50 in volume compression. This estimate represents a de-rating of the theoretically available $4^3=64$ compression. Moreover, it neglects the benefit of the resonance between the drive frequency and the natural plasma bounce frequency, described below. Nonetheless it is adequate for the purpose of illustration.

During the compression, the xenon ion density $n_i$ rises by a factor of 50, from $1\times10^{14}$ $cm^{-3}$ at maximum expansion to $5\times10^{15}$ $cm^{-3}$ at maximum compression. Simultaneously, the xenon plasma pressure p rises quasi-adiabatically as density $n_i$ to the 5/3 power, $p=Cn_i^{5/3}$. Temperature T rises as $p/n_i=Cn_i^{2/3}$, i.e., by a factor of 10, from 7 eV to 70 eV. Assumption of a factor 10 rise in temperature represents a de-rating of the theoretically available factor of 50213=14, to account for the loss of internal energy by radiation and thermal conduction. The plasma beta ($\beta=2\mu_0 p/B^2$) swings from 0.2 at maximum expansion to 6.7 in the center at maximum compression. The plasma beta transiently rises above unity in the center, as a feature of the nonlinear spherical compression wave.

At peak compression, the xenon plasma radiates efficiently and undergoes radiative collapse. The 13.45-nm EUV radiation this plasma produces is estimated as follows. The xenon plasma 13.45-nm EUV emissivity, per electron, per ion, has a maximum at a temperature T=70 eV, for ion densities $n_i<3\times10^{16}$ $cm^{-3}$. For this temperature and these densities, the 13.45-nm emissivity is $\epsilon=(2\times10^{-28}$ $Wcm^3/sr)$ $n_e$ $n_i$, where $n_e$ and $n_i$ the electron and ion densities (number per cubic cm), respectively. Under these conditions, the xenon average ionization state is 10, so $n_e=10n_i$. As the plasma is compressed, the ion density in the central region rises by a factor of 50, from $1\times10^{14}$ $cm^{-3}$ to $5\times10^{15}$ $cm^{-3}$. Correspondingly, the power of the 13.45-nm EUV radiation emitted from the central mm diameter region rises from the watt level to the kilowatt level. In the last 20 ns of compression, most of the thermal energy (millijoules) of the compressed plasma leaves as radiation (of all wavelengths) from a mm-diameter plasma bright spot. The local loss of internal energy by radiation drains the pressure of the central plasma region, resulting in radiative collapse. This positive feedback between radiation and compression results in significantly greater compression than if the plasma did not radiate. The average 13.45 nm EUV radiation power during the compression is 1 kW, with the average power over the whole cycle half that. The average 13.45-nm EUV power out is adjusted to 460 W, consisting of 3 million pulses per second, each containing 0.15 mJ of EUV energy.

As will be appreciated by those skilled in the art, a 13.45-nm EUV source as disclosed herein, with an effective EUV collection solid angle of $\pi$ sr, satisfied the need in 13.45-nm EUV semiconductor microlithography, of 115 W in 3.3 $mm^2$sr etendue at the intermediate focus.

Figure 6:
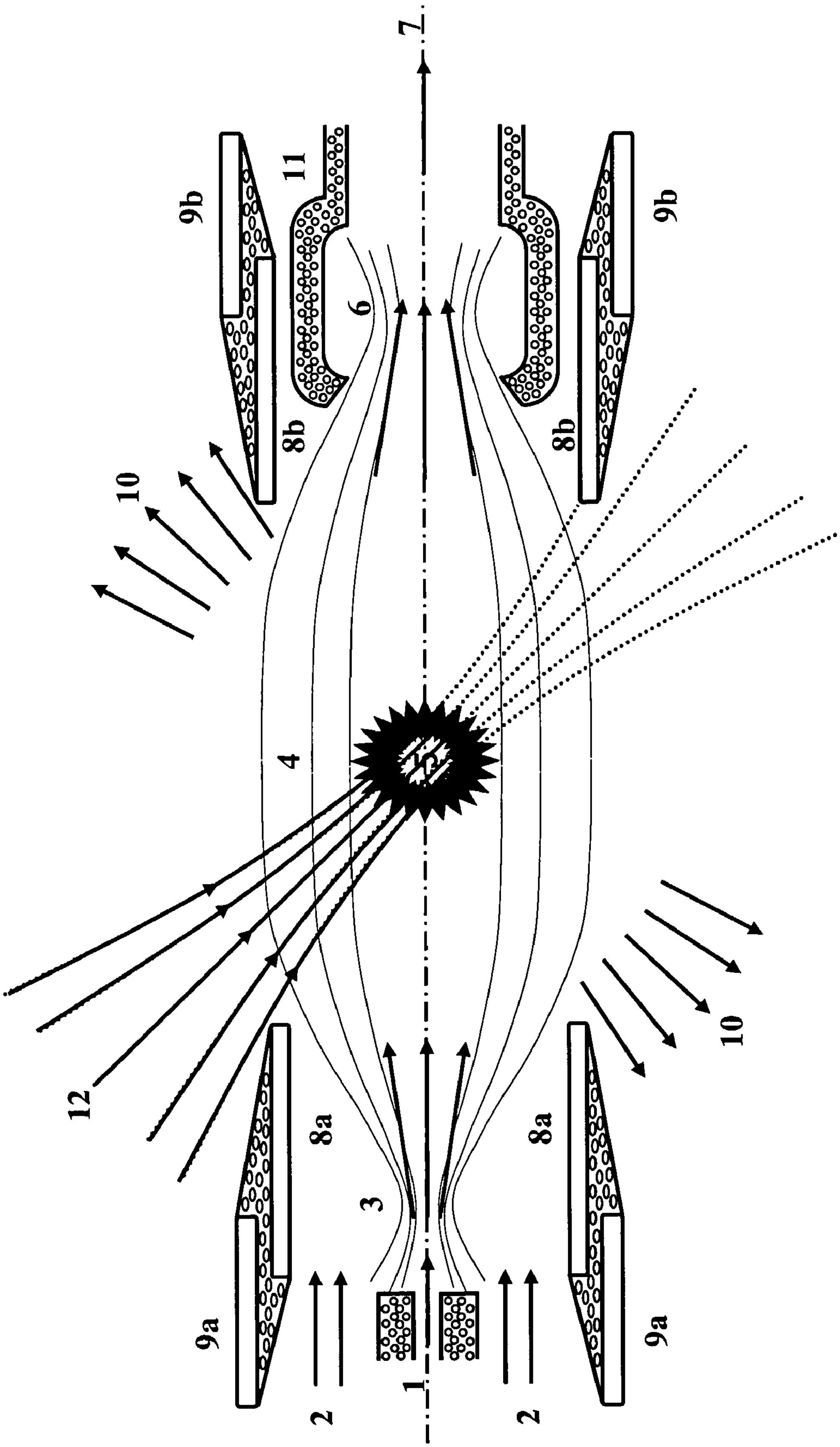
FIG. 6 is a conceptual diagram of an electrode-less light source configured with an additional optional short-pulse laser to drive population inversion and lasing of EUV light.

Alternatively, for selected EUV wavelengths, the efficiency and directionality of emissions can be increased by choosing the medium and device parameters to produce population inversion and EUV lasing, or by using an auxiliary intense, short-pulse laser to drive such conditions. FIG. 6 shows the device configured with an additional optional short-pulse laser. As in FIG. 1, the main device is cylindrically symmetric about the z-axis, indicated by a dashed line. The laser light 12 is focused on the dense plasma 5, with the focal spot preferably in the shape of a line along the direction that EUV laser light output 10 is desired. The laser beam comes from one side (it is not rotationally symmetric), and a cross-sectional view through the laser beam is shown. The line focus is obtained by means known in the art, such as, but not limited to, use of cylindrical optics or of spherical aberrations. The laser is preferably fired during the period, many nanoseconds long, that the oscillating plasma is at peak compression. In a fraction of a nanosecond, the laser light heats electrons in the assembled plasma via inverse bremsstrahlung (collisional absorption). The hot electrons excite ions, creating population inversions. The EUV lasing gain is maximum along the greatest length of excited plasma, i.e., along the line focus, which is perpendicular to the laser wavevector. The other elements in FIG. 6 are, as before, the radiation-source-material input nozzle 1, an optional buffer-gas input flow 2, a mirror-magnetic-field confined plasma from reference numeral 3 to reference numeral 6, magnetic field 4, an evacuation port 7, theta-pinch coils 8*a* and 8*b*, mirror-field coils 9*a* and 9*b*, and a mirror-throat plasma and debris dump 11.

After compression and radiation, the magnetic field falls and the plasma expands, returning energy to the circuit. On expansion, the plasma may cool to less than the 7 eV starting temperature, but is warmed to 7 eV by resistive (Ohmic) heating or by an auxiliary heating system (e.g., an electron beam). Partial inflow of new plasma (possibly influenced by a preionization system as described above) helps restore the plasma to a state optimized for re-implosion.

The oscillation or pulse frequency of the electrical circuit is matched to the natural bounce frequency of the plasma, to yield an efficient, repetitively pulsed EUV source, with a repetition rate of 3 MHz, for the example described here. The natural bounce frequency of the plasma is 3 MHz, estimated as follows. The implosion time is ~(3 mm)/$v_A$, where the average Alfven velocity $v_A=B/(\mu_0\rho)^{1/2}$~18 km/s as the magnetic field and xenon ion density (B, $n_i$) rise from (0.12 T, $1\times10^{14}$ $cm^3$) to (0.48 T, $5\times10^{15}$ $cm^{-3}$). Here $\rho=M_{Xe}n_i$ is the plasma mass density, where $M_{Xe}$ is the mass of a xenon atom. The round-trip time (the cycle period $\tau$) is double the implosion time, $\tau$~(6 mm)/$v_A$~0.33 µs, and the plasma bounce frequency is $f=1/\tau$~3 MHz. The resonance between the drive frequency and the natural plasma bounce frequency increases the plasma compression, compared with single-shot compression with the same amplitude drive. The reason is that in expanding from peak density, the plasma gains outward momentum and overshoots its equilibrium location. This induces diamagnetic currents in the plasma that reduce the magnetic field in the center and provide a restoring force that adds to the push of the driver in the subsequent re-implosion.

The parameters of the electrical circuit are as follows, for the rf-driven theta-pinch coils 8*a* and 8*b*. Energy oscillates between a capacitor and the theta-pinch coils, which serve as the inductor for the LC tank circuit. A peak total current of I=5.7 kA is split between the two coils. As the effective solenoid length is 1~4 cm, the peak magnetic field produced is $B$~$\mu_0 I/l$~0.18 T. The total inductance of the two coils, as an R~7-mm radius, 1~4-cm length solenoid is $L$~$\mu_0\pi R^2/l$~5 nHy. The magnetic energy stored at peak current by the coils is $U=IL^2/2$~80 mJ. The current is made to oscillate at the natural bounce frequency of the plasma, f~3 MHz. A capacitor tuned to C~0.6 µF sets the LC circuit oscillation period $\tau=2\pi(LC)^{1/2}$~0.33 µs=1/f. The voltage on the capacitor swings to a peak of V=500 V, for energy storage of $CV^2/2$~80 mJ. Each cycle, 5% (i.e., 4 mJ) of this stored energy is resistively converted to heat in the coils (an inductor rf quality factor $Q=2\pi/0.05=126$, at 3 MHz, is obtained using a helical resonator, or litzendraht conductor (litz wire), or other techniques known in the art). This (4 mJ)/(333 ns)=12 kW rf heat load is removed by the 1 kW/$cm^2$ cooling of the two coils. The rf input power to the LC tank circuit is 50 kW (25 mJ/cycle), with 12 kW resistively converted to heat in the coils, 30 kW going to plasma heating (15 mJ/cycle), and 8 kW lost elsewhere. The high fraction of throughput power makes appropriate use of the rf amplifier.

The rf input power is sufficient to deliver 115 W of 13.45-nm EUV to an intermediate focus. With a 1.5% conversion efficiency of 30-kW rf-plasma heating to 13.45-nm EUV radiation, 460 W of 13.45-nm EUV are generated. With an effective EUV collection solid angle of $\pi$ sr, 115 W of 13.45-nm EUV are delivered to the intermediate focus. The anticipation of a conversion efficiency of 1.5% is justified as follows. Efficiencies of prior-art 13.45-nm EUV sources of 1% (for xenon) and 3% (for tin) have been reported. However, greater efficiency is anticipated for the continuously driven plasma source described here, as compared to prior-art repetitive sources, in which the plasma is discarded after each radiation burst. There are several reasons for this. First, the quasi-spherical implosion and resonance results in less lost plasma translational energy. Second, the reutilization of multicharged xenon ions spreads the significant energy cost of ionization over several EUV emission cycles. Last, some energy is recovered from the plasma each cycle by the electrical circuit.

In addition to being useful as a single source, the electrodeless discharge EUV source described here can be combined with one or more similar sources to provide an array of sources producing EUV light that is combined to provide a single combined EUV light source, for applications such as integrated circuit lithography.

While embodiments and applications of this disclosure have been shown and described, it would be apparent to those skilled in the art that many more modifications and improvements than mentioned above are possible without departing from the inventive concepts herein. The disclosure, therefore, is not to be restricted except in the spirit of the appended claims.

What is claimed is:

1. An electrode-less discharge extreme ultraviolet light source, comprising:

a vacuum vessel;

an input nozzle disposed within the vessel along an axis, the input nozzle being configured to input material along the axis from which radiation is desired;

an evacuation port disposed along the axis and spaced apart from the input nozzle;

a first theta-pinch coil disposed radially about the axis proximate to the input nozzle;

a second theta-pinch coil disposed radially about the axis proximate to said evacuation port;

a first mirror-field coil disposed radially about the axis proximate to the input nozzle;

a second mirror-field coil disposed radially about the axis proximate to the evacuation port;

the first theta-pinch coil being disposed between the first mirror-field coil and the axis, and the second theta-pinch coil being disposed between the second mirror-field coil and the axis;

the first and second theta pinch coils and the first and second mirror-field coils being driven so as to form and heat a plasma about a position midway between the input nozzle and the evacuation port, thereby emitting radiation at the midway position.

2. The electrode-less discharge extreme ultraviolet light source of claim 1 wherein the first and second theta pinch coils and the first and second mirror-field coils are driven to heat the plasma by alternately compressing and expanding it.

3. The electrode-less discharge extreme ultraviolet light source of claim 2 wherein said theta-pinch coils compress the plasma in a spherical or quasi-spherical manner.

4. The electrode-less discharge extreme ultraviolet light source of claim 2 wherein said theta-pinch coils compress the plasma in a cylindrical or quasi-cylindrical manner.

5. The electrode-less discharge extreme ultraviolet light source of claim 2 wherein said theta-pinch coils compress the plasma in a pancake-like manner.

6. The electrode-less discharge extreme ultraviolet light source of claim 1 wherein the ratio of theta-pinch heating power to plasma mass is such that ohmic heating of the plasma exceeds compressional heating.

7. The electrode-less discharge extreme ultraviolet light source of claim 1 wherein the wavelengths and intensity of the emitted radiation are selected by the choice of the radiating material.

8. The electrode-less discharge extreme ultraviolet light source of claim 1 wherein the gas contains one of lithium, tin, and xenon for the production of EUV of wavelength around 13 nm.

9. The electrode-less discharge extreme ultraviolet light source of claim 1 wherein the input nozzle is tailored to provide selected gas flow characteristics.

10. The electrode-less discharge extreme ultraviolet light source of claim 4 wherein the input nozzle is a Laval nozzle.

11. The electrode-less discharge extreme ultraviolet light source of claim 1 wherein the input nozzle is a dynamic gas puff valve.

12. The electrode-less discharge extreme ultraviolet light source of claim 1 and further comprising a sputtering or laser-deposition means for producing said gas from solid, liquid, or porous material.

13. The electrode-less discharge extreme ultraviolet light source of claim 1 wherein said nozzle comprises one of a pellet injector and a droplet injector for providing the gas.

14. The electrode-less discharge extreme ultraviolet light source of claim 1 and further comprising a preionizer for converting said gas into plasma as it is injected into the central volume.

15. The electrode-less discharge extreme ultraviolet light source of claim 14 wherein said preionizer is selected from the group including a high-voltage pin, an electron beam, a laser, a radio-frequency source, an ultraviolet light source.

16. The electrode-less discharge extreme ultraviolet light source of claim 9 wherein said preionizer is built into the package surrounding said input nozzle.

17. The electrode-less discharge extreme ultraviolet light source of claim 1 and further comprising a plasma initiating device for initially converting said gas into plasma in the central volume.

18. The electrode-less discharge extreme ultraviolet light source of claim 1 wherein the plasma initiating device is selected from the group including a high-voltage pin, an electron beam, a laser, a radio-frequency source, an ultraviolet light source.

19. The electrode-less discharge extreme ultraviolet light source of claim 1 wherein said gas is enveloped by a buffer gas.

20. The electrode-less discharge extreme ultraviolet light source of claim 19 wherein said buffer gas is helium or another noble gas.

21. The electrode-less discharge extreme ultraviolet light source of claim 1 wherein the mirror magnetic field is stronger toward said input nozzle than toward said evacuation port, so that plasma flows gently to said evacuation port.

22. The electrode-less discharge extreme ultraviolet light source of claim 1 and further comprising means for generating Ioffe currents for increased stability of the mirror plasma confinement.

23. The electrode-less discharge extreme ultraviolet light source of claim 1 wherein said mirror-field coils are superconducting.

24. The electrode-less discharge extreme ultraviolet light source of claim 1 wherein said evacuation port is fitted with a plasma and debris dump.

25. The electrode-less discharge extreme ultraviolet light source of claim 24 wherein said debris dump in the shape of one of a cavity and a cone that opens away from the plasma.

26. The electrode-less discharge extreme ultraviolet light source of claim 25 and further comprising a device for producing a magnetic field, included in the package surrounding said plasma and debris dump.

27. The electrode-less discharge extreme ultraviolet light source of claim 26 wherein said device comprises a magnet.

28. The electrode-less discharge extreme ultraviolet light source of claim 27 wherein said magnet is at least one of a current-carrying coil, ferromagnetic material and permanent magnets.

29. The electrode-less discharge extreme ultraviolet light source of claim 1 wherein said theta-pinch coils are constructed so as to have a high quality factor Q.

30. The electrode-less discharge extreme ultraviolet light source of claim 29 wherein said theta-pinch coils are constructed from one of a litzendraht conductor (litz wire) and a helical resonator.

31. The electrode-less discharge extreme ultraviolet light source of claim 1 wherein said theta-pinch coils are part of a circuit capable of efficiently driving a large current.

32. The electrode-less discharge extreme ultraviolet light source of claim 31 wherein said circuit is one of a radiofrequency-driven circuit, resonant LC-tank circuit, and a circuit that recovers energy reflected from said theta-pinch coils.

33. The electrode-less discharge extreme ultraviolet light source of claim 21 wherein the theta-pinch frequency is tuned to the natural plasma bounce frequency to enhance the plasma oscillation and compression.

34. The electrode-less discharge extreme ultraviolet light source of claim 33 wherein the theta-pinch current pulse shape is adjusted to maximize the plasma compression.

35. The electrode-less discharge extreme ultraviolet light source of claim 1 and further comprising electrostatic shielding, included in the theta-pinch coil package, both inside and outside the coil.

36. The electrode-less discharge extreme ultraviolet light source of claim 1 and further comprising heat pipes for cooling at least said theta-pinch coils, said mirror coils, said input nozzle, said evacuation port, through which flow coolant.

37. The electrode-less discharge extreme ultraviolet light source of claim 36 wherein said heat pipes are connected to regions that are structured for high heat removal including one of microchannels and porous, high-thermal-conductivity heat-exchange matrix.

38. The electrode-less discharge extreme ultraviolet light source of claim 1 wherein plasma-facing components are treated or coated with plasma-resistant materials to minimize debris and promote component life.

39. The electrode-less discharge extreme ultraviolet light source of claim 38 wherein said plasma resistant materials are selected from the group including diamond and boron.

40. The electrode-less discharge extreme ultraviolet light source of claim 1 and further comprising EUV collection and transport optics.

41. The electrode-less discharge extreme ultraviolet light source of claim 1 and further comprising debris and/or spectral filters, in the direction of EUV collection, as are known in the art, such as, but not limited to, thin membranes, gas jets, plasmas, and capillaries that are differentially pumped and/or contain buffer gas.

42. The electrode-less discharge extreme ultraviolet light source of claim 1 and further comprising an intense short-pulse laser to drive population inversion and EUV lasing.

43. The electrode-less discharge extreme ultraviolet light source of claim 34 wherein said intense short-pulse laser is focused to a spot that has the shape of a line.

44. The electrode-less discharge extreme ultraviolet light source of claim 1 wherein said source is combined with one or more similar sources to provide an array of sources producing EUV light that is combined to provide a single combined EUV light source.

* * * * *